(12) United States Patent
Kuebler

(10) Patent No.: US 9,023,346 B2
(45) Date of Patent: May 5, 2015

(54) METHOD OF TREATING STROKE WITH TENECTEPLASE

(75) Inventor: Peter Kuebler, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 530 days.

(21) Appl. No.: 13/189,413

(22) Filed: Jul. 22, 2011

(65) Prior Publication Data

US 2012/0164157 A1    Jun. 28, 2012

Related U.S. Application Data

(63) Continuation of application No. 11/832,291, filed on Aug. 1, 2007, now abandoned.

(60) Provisional application No. 60/823,868, filed on Aug. 29, 2006.

(51) Int. Cl.
| | | |
|---|---|---|
| *A61K 38/43* | (2006.01) | |
| *A61K 38/49* | (2006.01) | |
| *A61K 9/00* | (2006.01) | |
| *A61K 9/08* | (2006.01) | |

(52) U.S. Cl.
CPC ............... *A61K 38/49* (2013.01); *A61K 9/0019* (2013.01); *A61K 9/08* (2013.01)

(58) Field of Classification Search
None
See application file for complete search history.

(56) References Cited

U.S. PATENT DOCUMENTS

| | | |
|---|---|---|
| 2003/0180282 A1 | 9/2003 | Serebruany et al. |
| 2004/0029798 A1 | 2/2004 | Armstrong et al. |
| 2007/0014779 A1 | 1/2007 | Semba |
| 2008/0107641 A1 | 5/2008 | Kuebler |

FOREIGN PATENT DOCUMENTS

| | | |
|---|---|---|
| WO | WO-93/24635 A1 | 12/1993 |
| WO | WO-2006/094120 A2 | 9/2006 |
| WO | WO-2006/094120 A3 | 9/2006 |
| WO | WO-2008/027687 A2 | 3/2008 |
| WO | WO-2008/027687 A3 | 3/2008 |

OTHER PUBLICATIONS

Van de Werf et al., The Lancet 1999, 354:716-22.*
Chapman, D.F. (2000). "Incidence of Cerebral Hemorrhage and Thrombolysis Following Treatment with TNK or tPA in a Rabbit Model of Thromboembolic Stroke," *Neurology* 54(7-Suppl. 3):A261.
Guptu, V.K. (2004). "Intravenous Magnesium for Neuroprotection in Acute Stroke: Clinical Hope Versus Basic Neuropharmacology," *Stroke* 35:2758-2759.
Haley, Jr. E.C. et al. (2005). "A Pilot Dose-Escalation Safety Study of Tenecteplase in Acute Ischemic Stroke," *Stroke* 36(3):607-612.
International Search Report mailed Feb. 14, 2008, for PCT Application No. PCT/US2007/074997, filed Aug. 1, 2007, seven pages.
Keyt, B.A. et al. (1994). "A Faster-Acting and More Potent Form of Tissue Plasminogen Activator," *Proc. Natl. Acad. Sci. USA* 91(9):3670-3674.
Lapchak, P.A. et al. (2004). "Comparison of Tenecteplase with Alteplase on Clinical Rating Scores Following Small Clot Embolic Strokes in Rabbits," *Experimental Neurology* 185(1):154-159.
O'Neil, M.J. et al. ed. (2001). Definition of "Tenecteplase" No. 9220 in *The Merck Index*, Thirteenth Edition, Merck & Co.: Whitehouse Station, NJ, p. 1631.
Sacco, R.L. et al. (2007). Experimental Treatments for Acute Ischaemic Stroke, *The Lancet* 369(9558):331-341.
Semba, C.P. et al. (2001). Alteplase and Tenecteplase: Applications in the Peripheral Circulation, *Techniques in Vascular and Interventional Radiology* 34(2):99-106.
Thomas, G.R. et al. (1994). "A Long-Half-Life and Fibrin-specific Form of Tissue Plasminogen Activator in Rabbit Models of Embolic Stroke and Peripheral Bleeding," *Stroke, American Heart Association* 25(10):2072-2078.
Zhang, R.L. et al. (2000). "Postischemic Intracarotid Treatment with TNK-tPA Reduces Infarct Volume and Improves Neurological Deficits in Embolic Stroke in the Unanesthetized Rat," *Brain Research* 878(1-2):64-71.

* cited by examiner

*Primary Examiner* — Sharon Wen
(74) *Attorney, Agent, or Firm* — Morrison & Foerster LLP

(57) ABSTRACT

A method for treating acute ischemic stroke in a human comprises administering tenecteplase to the human in a total dose of about 0.05 to 0.5 mg/kg, given as (a) an initial bolus dose of about 0.015 to 0.15 mg/kg, followed by infusion of an amount equaling the total dose minus the initial dose over a period of about 50-90 minutes, or (b) a bolus. Also described are kits for carrying out this method.

14 Claims, 2 Drawing Sheets

METHOD OF TREATING STROKE WITH TENECTEPLASE

RELATED APPLICATION

The present application is a continuation of U.S. patent application Ser. No. 11/832,291 filed on 1 Aug. 2007, which claims the benefit to U.S. Provisional Patent Application Ser. No. 60/823,868 filed on 29 Aug. 2006, the entire contents of which are hereby incorporated by reference.

BACKGROUND OF THE INVENTION

1. Field of the Invention

The invention is related to a method of treating stroke with a thrombolytic agent, more particularly, a method of administering tenecteplase in a certain dosing regimen to treat acute ischemic stroke.

2. Description of Related Art

Stroke is a general term for acute brain damage resulting from disease of the blood vessels. This presents a serious problem to society, with about 500,000 people dying from or becoming permanently disabled by stroke in the United States each year. Stroke can be classified into two main categories: hemorrhagic stroke (resulting from leakage of blood outside of the normal blood vessels) and ischemic stroke (cerebral ischemia due to lack of blood supply); this application is concerned with the latter.

Ischemic stroke is responsible for about one third of all deaths in industrialized countries and is the major cause of serious, long-term disability in adults over the age of 45. It stands to reason that there is a need for pharmacotherapy to treat acute ischemic stroke. Considerable insights have been gained into the mechanisms of stroke and the cascade of events that occurs following stroke; there is also an improved understanding of neuronal injury and cell death.

The three main mechanisms of ischemic stroke are thrombosis, embolism, and systemic hypoperfusion (with resultant ischemia and hypoxia). In each of these types of stroke, the area of the brain that dies as a result of the lack of blood supply thereto is called an infarct. Obstruction of a cerebral artery resulting from a thrombus that has built up on the wall of a brain artery is generally called "cerebral thrombosis." In cerebral embolism, the occlusive material blocking the cerebral artery arises downstream in the circulation (e.g., an embolus is carried to the cerebral artery from the heart). Because it is difficult to discern whether a stroke is caused by thrombosis or embolism, the term "thromboembolism" is used to cover both these types of stroke. Systemic hypoperfusion may arise as a consequence of elevated blood lactate levels, reduced hematocrit, low blood pressure, or inability of the heart to pump blood adequately.

When symptoms of stroke last less than 24 hours and the patient recovers completely, the patient is said to have undergone a transient ischemic attack (TIA). The symptoms of TIA are a temporary impairment of speech, vision, sensation, or movement. Because a TIA is often thought to be a prelude to full-scale stroke, patients having suffered a TIA are candidates for prophylactic stroke therapy with anticoagulation agents (e.g., coumarin, and heparin) or anti-platelet agents (such as aspirin and ticlopidine), for example.

Acute ischemic stroke (AIS) is a heterogeneous disease process; prediction of course, recovery, disability, or death is difficult. It is typically due to an acute thromboembolic arterial occlusive lesion. The location of the arterial occlusive lesion in acute ischemic stroke is relatively heterogeneous.

Thrombolytic agents, such as recombinant tissue plasminogen activator (rtPA), have been used in the treatment of thromboembolic stroke, and function by lysing the thrombus causing the ischemia. In fact, intravenous rtPA (alteplase, ACTIVASE®) is the only drug approved for the treatment of acute ischemic stroke. Intravenous rtPA (0.9 mg/kg, maximum 90 mg), with 10% of the dose given as a bolus followed by an infusion lasting 60 minutes, is recommended treatment within 3 hours of onset of ischemic stroke. This drug is believed to be most useful if administered as soon as possible after acute stroke (Gross et al., *Neurosurgery*, 36:1172-1177 (1995); Ingall et al., *Stroke*, 35: 2418-2424 (2004); The ATLANTIS, ECASS, and NINDS rt-PA Study Group Investigators, *Lancet*, 363: 768-774 (2004)), to restore, partially at least, cerebral blood flow in the ischemic region and to sustain neuronal viability. There is additional evidence, however, that administration at later times, by means of other methods, is effective, for example, by use of diffusion-weighted and perfusion MR imaging techniques and CT perfusion technology. Tomsick, *J. Vase. Interv. Radiol.*, 15: S67-S76 (2004). In addition, catheter-based treatment with intra-arterial tissue-plasminogen activator (tPA) or urokinase alone or with adjuvant balloon angioplasty/stenting for those patients ineligible for intravenous treatment of acute ischemic stroke has been successful. Ramee et al., *Stroke*, 35: e109-e111 (2004). A combined intravenous and intra-arterial tPA approach to recanalization in ischemic stroke patients has also been proposed. The IMS Study Investigators, *Stroke*, 35: 904-912 (2004).

Thrombolysis, the lysis of a cerebral arterial clot with tPA within hours of symptom onset in ischemic stroke, has been approved for treatment of acute ischemic stroke since 1996. Two other agents, pro-urokinase (intra-arterial administration directly into M1 or M2 arterial thrombus) and intravenous ancrod, a fibrinogen-lowering agent derived from the venom of the Malayan pit viper, have shown therapeutic benefit, and may be available for acute ischemic stroke therapy in the future. The effect of anti-ICAM-1 antibodies in a rabbit embolic stroke model followed by thrombolysis with tPA has also been examined (Bowes et al., *Exp. Neurol.*, 119:215-219 (1993)). Although tPA (30 minutes post-ischemia) and anti-ICAM-1 antibody (five minutes post-ischemia) each separately improved the neurological outcome relative to controls, administration of a combination of the two compounds at the same time was no more effective than administering either compound alone. When thrombolysis was delayed three hours following embolism, neither tPA nor the combination reduced neurological damage. Experiments in rabbits have also shown that tPA (30 minutes post-ischemia) and an anti-CD18 antibody (5 minutes post-ischemia) each separately improved neurological outcome, although administration of the combination of the two compounds at the same time was no more effective than administering either compound alone (Bowes et al., *Neurology*, 45:815-819 (1995)). The combination of anti-ICAM-1 antibody (15 minutes post-ischemia) and tPA (2 hours post-ischemia) extended the pest-ischemia duration at which the tPA remained effective. That is, the combination was effective in extending the therapeutic window of tPA outside the effective therapeutic window of the tPA when administered alone in a rabbit. This effect has also been seen in rats with tPA and a glycoprotein IIB/IIIA receptor inhibitor. Li et al., *Circulation*, 107: 2837-2843 (2003). US Pat. Pubs. 2002/0081294 and US 2004/0057951 disclose co-administration of a thrombolytic compound and an anti-CD18 antibody for increasing blood flow in an infarct-related artery in a mammal such as a human (e.g., acute myocardial infarction (AMI) in a mammal with a blocked coronary artery or focal ischemic stroke caused by obstruction of a cerebral artery).

U.S. Pat. No. 6,541,452 discloses a brain-associated inhibitor of tPA and its use in treating stroke. US Pat. Pub. 2004/0176347 discloses a pharmaceutical composition for treating cerebral ischemic diseases comprising an astrocyte-function-improving agent and a thrombolytic agent, preferably tPA, as active ingredients.

Tenecteplase (TNK, TNKASET™, Genentech, Inc., South San Francisco, Calif.) is a genetically engineered variant of human tPA cloned and expressed in Chinese hamster ovary cells. Keyt et al., *Proc. Natl. Acad. Sci USA*, 91: 3670-3674 (1994). See also Verstraete, *Am. J. Med*, 109: 52-58 (2000) for an overview of third-generation thrombolytic drugs in general. Approved in the U.S. for a single-bolus administration in patients with AMI, tenecteplase was engineered to have increased fibrin specificity and an increased half-life compared to alteplase.

Tenecteplase and alteplase were equivalent for 30-day mortality when single-bolus tenecteplase was compared with front-loaded alteplase in acute myocardial infarction in the ASSENT-2 double-blind randomized trial. The ease of administration of tenecteplase may facilitate more rapid treatment in and out of the hospital. Van de Werf et al., *Lancet*, 354: 716-722 (1999). The results of the ASSENT-2 study indicated that total stroke rate and 30-day mortality were lower in female patients over 75 years of age treated with tenecteplase than in those treated with alteplase, albeit that the difference was statistically not significant. The authors concluded that female patients and patients over 75 years of age will probably benefit more from a thrombolytic agent that is given according to a weight-adjusted close regimen, e.g., tenecteplase. Vermeer, *Thrombosis Research*, 103: Supplement 1, S101-S104 (Sep. 30, 2001). Other thrombolytic drugs that may be useful in treating AMI include streptokinase, urokinase, anistreplase, alteplase, saruplase, reteplase, lanoteplase, staphylokinase, fibrolase, prourokinase, and vampire bat plasminogen activator. Iqbal, *Clinical and Applied Thrombosis/Hemostasis*, 6/1: 1-13 (2000). Follow-up data with tenecteplase indicate that it shows overall efficacy and tolerability profiles similar to those of alteplase, with comparable mortality after one year of follow-up. Tenecteplase has an apparent advantage over alteplase in reduced mortality in patients receiving late treatment and reduced incidence of non-cerebral bleeding complications in ASSENT-2. Dunn and Goa, *Am J Cardiovasc Drugs* 1 (1), 51-66 (2001).

Callahan et al., *HeartDrug* 1/5: 281-290 (2001) is a review stating that both r-PA and tenecteplase are effective in treating AMI when given as bolus therapy, a feature that may facilitate earlier treatment initiation as well as lower treatment costs. In a later study it was found that the thrombolytic drugs (reteplase, tenecteplase, alteplase, and streptokinase) appear to be of similar efficacy in reducing mortality, and the apparent benefits of accelerated alteplase in GUSTO-I are consistent with this. Dundar et al., *QJM*, 96: 103-113 (2003). Tenecteplase was found to be effective in treating AMI in combination with the low-molecular-weight heparin enoxaparin (ENOX) or unfractionated heparin in the prehospital setting in a trial called ASSENT-3 PLUS. The combination of tenecteplase with ENOX reduces early ischemic events, but lower doses of ENOX need to be tested in elderly patients. Wallentin et al., *Circulation*, 108: 135-142 (2003); U.S. Pat. No. 7,084,118.

In the treatment of ischemic stroke, Jonas et al., *Annals of the New York Academy of Sciences*, 939: 257-267 (2001) discloses the predictive value of animal models in assessing the failure of neuronal protective agents versus the success of thrombolysis. Agents claimed to be neuroprotective in animal stroke models have all failed in human trials. Thrombolysis has been reported as beneficial in animal and human stroke. In animals the effect of neuroprotective agents and of thrombolytic agents on infarct size is time-dependent: early initiation of treatment works best; and benefit is progressively—and eventually totally—lost with increasing delay of time of first treatment. The animal data also show that, overall, the beneficial effects of the neuroprotective agents are weaker, and are totally lost sooner, than those of thrombolytics. The human data show that the failed trials of the neuroprotective agents had entry windows that went far beyond the windows of (any) success seen in tests of these agents in animals. By contrast, human thrombolysis trials uniformly restricted time of entry to windows in which these agents have shown beneficial effect in animals. In clinical stroke trials, neuroprotective agents failed to produce benefit because their effects at best are too weak, and they were used at times predictable from the animal models as too late. Thrombolytic therapy, such as tenecteplase and urokinase, which has a stronger-effect than neuroprotective agents in animal models, was used clinically during the early window of optimal effectiveness, and produced beneficial results.

The field of intravenous and intra-arterial thrombolysis for the treatment of acute ischemic stroke is rapidly advancing. Limitations of existing thrombolytic agents have prompted the development of new thrombolytic agents over the last decade, called third-generation thrombolytics. Two of the several third-generation thrombolytic agents have been investigated for the treatment of acute ischemic stroke and include tenecteplase and reteplase. By virtue of structural modifications, third-generation thrombolytics have longer half-lives and greater penetration into the thrombus matrix. The first prospective human clinical trial evaluated the safety and efficacy of intra-arterial reteplase in 16 patients with ischemic stroke who were poor candidates for intravenous alteplase therapy. Near complete or complete recanalization was observed after treatment in 88% of the patients. The development and use of third-generation thrombolytics is expected to increase the rate of recanalization and clinical recovery in patients with ischemic stroke. Qureshi et al., *Current Opinion in Investigational Drugs* 3(12): 1729-1732 (2002).

For example, monteplase, a modified rtPA, reduces infarct volume and hemorrhagic transformation in rat model of embolic stroke. Muramatsu et al., *Neurological Research*, 24: 311-316 (2002). Other such third-generation drugs include lanoteplase, plasmin, or a truncated form of plasmin (microplasmin), a direct-acting thrombolytic with non-thrombolytic-related neuroprotective, therapeutic activities, recombinant desmodus rotundus salivary plasminogen activator (rDSPA) alpha-1, and a mutant fibrin-activated human plasminogen (BB10153; British Biotech Inc.). These areas of drug discovery and development are reviewed in Lapchak, *Expert Opinion on Investigational Drugs* 11: 1623-1632 (2002).

A multi-center, randomized, double-blinded sequential dose-escalation clinical trial called the CLEAR stroke study is now being conducted to evaluate the safety of eptifibatide, an intravenous cyclical heptapeptide that selectively blocks the platelet glycoprotein IIb/IIIa receptor, in combination with low-dose rtPA in acute ischemic stroke treated within three hours.

It has been proposed that tenecteplase may be neuroprotective following a stroke because of its increased fibrin specificity over alteplase, its resistance to PAI-1, and its increased biological half-life (18 vs. 10 minutes for alteplase), features that could lead to fewer cerebral hemorrhages than alteplase in stroke patients.

A pilot study of tenecteplase was made in 88 acute ischemic stroke patients enrolled over 2000 to 2003 using four dose tiers of tenecteplase: 0.1, 0.2, 0.4, and 0.5 mg/kg. There were no symptomatic intracranial hemorrhages (ICHs) in the first three tiers. Two of 13 patients had symptomatic ICH at 0.5 mg/kg, and there were increasing ICHs with increasing doses (8%-38%), with outcomes similar to the alteplase group in the earlier acute ischemic stroke trial. Tenecteplase is currently being tested in a randomized controlled Phase IIb clinical study in acute ischemic stroke patients using 0.1 mg/kg tenecteplase, 0.4 mg/kg tenecteplase, and 0.9 mg/kg rtPA.

In an early animal study, the activity of tenecteplase was compared with that of alteplase in rabbit models of embolic stroke and peripheral bleeding. Infusion of alteplase or bolus administration of the tenecteplase resulted in dose-dependent clot lysis. The tenecteplase was found to be an order of magnitude more potent than alteplase on a milligram-per-kilogram basis. Unlike alteplase, tenecteplase caused less systemic activation of plasminogen and fewer hemorrhagic transformations in this model. The tenecteplase did not extend template bleeding times. The authors state that by combining increased fibrin specificity with decreased plasma clearance, it is possible to produce a thrombolytic agent (tenecteplase) that is more convenient and more potent than wild-type tPA. According to the authors, the significant reduction in hemorrhagic conversions may be attributable to the conservation of systemic plasminogen seen with this molecule. Thomas et al., *Stroke,* 25: 2072-2078 (1994).

In another animal study, tenecteplase in a dose of using 0.6 mg/kg or 1.5 mg/kg was compared with wild-type tPA in a rabbit embolic stroke model. Both wild-type tPA and tenecteplase caused thrombolysis in most subjects, and did not differ from each other. Neither tenecteplase nor tPA affected the size of the hemorrhages. Tenecteplase shows comparable rates of recanalization compared with wild-type tPA in a model of embolic stroke. While tPA increases hemorrhage rate, the hemorrhage associated with tenecteplase treatment is not statistically different compared with controls or the tPA group. The authors suggested that tenecteplase shows promise as an alternative thrombolytic treatment for stroke, but they could not demonstrate improved safety compared with wild-type tPA. Chapman et al., *Stroke,* 32: 748-52 (2001).

More recent studies in humans indicate many parallels with animal studies, not only in the nature of events following ischemia, but also in their time course. Callaway, *Current Neuropharmacology,* 2/3: 277-294 (2004). Co-administration of NXY-059 (100 mg/kg) and tenecteplase (0.9 mg/kg) six hours following embolic strokes in rabbits improves clinical rating scores. Lapchak et al., *Experimental Neurology* 188: 279-285 (August 2004); *Comment in Exp Neurol.,* 188: 195-199 (August 2004). Wagner and Jauch *Experimental neurology* 188 (2): 195-199 (2004); *Comment on Exp Neurol.* 188(2) 279-85(2004) discloses the window for acute stroke treatment of thrombolytics such as tenecteplase plus central-nervous-system (CNS)-protective therapies such as free-radical scavengers, NXY 059, and nitrogen oxides. Lapchak et al., *Experimental Neurology,* 185: 154-159 (2004) discloses a comparison of tenecteplase with alteplase on clinical rating scores following small-clot embolic strokes in rabbits. The rabbit small clot embolic stroke model (RSCEM) was used for a dose-response profile analysis of tenecteplase (0.1 mg/kg-3.3 mg/kg) and alteplase (0.9 mg/kg-3.3 mg/kg) given intravenously 1 hour following embolization.

In additional studies, tenecteplase (0.9 mg/kg) or alteplase (3.3 mg/kg) was administered 3 (or 6) hours following embolization to determine the therapeutic window for the thrombolytics. For both studies, behavioral analysis was conducted 24 hours following embolization, allowing for the determination of the effective stroke dose (P50) or clot amount (mg) that produces neurological deficits in 50% of the rabbits.

This study indicates that tenecteplase has a wide therapeutic range, a therapeutic window of at least 3 hours, and a durable effect. Moreover, the safety profile for tenecteplase is similar to that of alteplase. Tenecteplase does not increase the rate of intracerebral hemorrhage (ICH) above that produced by alteplase. However, the therapeutic range and window for alteplase is more limited than that for tenecteplase. These preclinical studies suggest that tenecteplase has a better pharmacological profile than alteplase and supports further investigation of tenecteplase in randomized double-blinded clinical trials in stroke patients. Sec also Araujo et al., *Society for Neuroscience Abstract Viewer and Itinerary Planner,* Volume: 2003, Page: Abstract No. 102.2 (2003) Conference: 33rd Annual Meeting of the Society of Neuroscience, New Orleans, La., USA, Nov. 8-12, 2003.

There is a need to provide a method for improving clinical outcome in acute ischemic stroke, such as by increasing cerebral blood flow and/or reducing infarct size, using tenecteplase.

SUMMARY OF THE INVENTION

Accordingly, the invention is as claimed. In one aspect, the invention provides a method for treating acute ischemic stroke in a human comprising administering tenecteplase to the human in a total dose of about 0.05 to 0.5 mg/kg, given as (a) an initial bolus dose of about 0.015 to 0.15 mg/kg, followed by infusion of an amount equaling the total dose minus the initial dose over a period of about 50-90 minutes, or (b) a bolus only. Conveniently, tenecteplase is administered to the human in the form of a pharmaceutically acceptable formulation, such as those elaborated in more detail herein. Preferably, the total dose is about 0.2 to 0.3 mg/kg, more preferably about 0.25 mg/kg.

In one embodiment of this method, the total dose is given as an initial bolus followed by the infusion. Preferably, the initial dose is about 0.08 to 0.12 mg/kg, more preferably about 0.1 mg/kg bolus, and/or the period of infusion is about 55-70 minutes, more preferably about 60 minutes. In a particularly preferred embodiment, the total dose is about 0.25 mg/kg, given as an initial about 0.1 mg/kg bolus, followed by infusion of about 0.15 mg/kg over about 60 minutes. In another particularly preferred embodiment, tenecteplase is administered to the human in a total dose of about 0.25 mg/kg in about 60 minutes, given as an initial bolus of about 0.1 mg/kg over one minute, followed by infusion of about 0.25 mg/kg for the rest of about 60 minutes.

In another embodiment of this method, the total dose is given as a bolus only. The total dose typically is about 0.05 to about 0.5 mg/kg. In a preferred embodiment, the total dose is about 0.25 mg/kg.

Preferably in both methods, the tenecteplase is administered to the human at a time between about 15 minutes to about 20 hours from the onset of acute ischemic stroke, more preferably between about 45 minutes to about 6 hours, and still more preferably up to no more than about 3 hours from the onset of acute ischemic stroke. In a preferred embodiment, the bolus is intravenous and/or the infusion is continuous.

In a preferred embodiment of both these methods, they further comprise administering to the human an effective amount of a second medicament, wherein the first medicament is tenecteplase. This second medicament is preferably a neuroprotective agent, a thrombolytic agent, a glycoprotein IIb IIIa antagonist, or an anti-CD18 antibody. This second medicament may be co-administered to the human either before, after, or simultaneously with, the tenecteplase. Such second medicament, for example, may be administered to the mammal more than about 3 hours after the onset of ischemic stroke (e.g., at least once within about 3-8 hours and preferably within about 3-6 hours from the onset of stroke).

In another aspect, the invention supplies a kit comprising: a container comprising tenecteplase; and instructions for using the tenecteplase to treat acute ischemic stroke in a human by administering the tenecteplase to the human in a total dose of about 0.05 to 0.5 mg/kg, given as (a) an initial bolus dose of about 0.015 to 0.15 mg/kg, followed by infusion of an amount equaling the total dose minus the initial dose over a period of about 50-90 minutes, or (b) a bolus.

Preferably, the total dose is about 0.2 to 0.3 mg/kg, more preferably about 0.25 mg/kg, and the initial bolus is about 0.08 to 0.12 mg/kg.

In one embodiment of the kit, the total dose is given as an initial bolus followed by the infusion. In a preferred embodiment, the total dose is about 0.25 mg/kg, given as an initial about 0.1 mg/kg bolus, followed by infusion of about 0.15 mg/kg over 60 minutes. In a particularly preferred embodiment of the kit, the total dose is about 0.25 mg/kg, given as an initial about 0.1 mg/kg bolus, followed by infusion of about 0.15 mg/kg over about 60 minutes. In another particularly preferred embodiment of the kit, tenecteplase is given in a total dose of about 0.25 mg/kg in about 60 minutes, given as an initial bolus of about 0.1 mg/kg over one minute, followed by infusion of about 0.25 mg/kg for the rest of 60 minutes.

In another embodiment of the kit, the total dose is given as a bolus only.

The kits herein preferably further comprise a container comprising a second medicament, wherein the instructions include instructions for using the second medicament in combination with the tenecteplase to treat ischemic stroke in a human by administering to the human an effective amount of the second medicament. The preferred second medicament is a neuroprotective agent, a thrombolytic agent, a glycoprotein IIb IIIa antagonist, or an anti-CD18 antibody.

DETAILED DESCRIPTION OF THE PREFERRED EMBODIMENTS

A. Definitions

Figure 1:
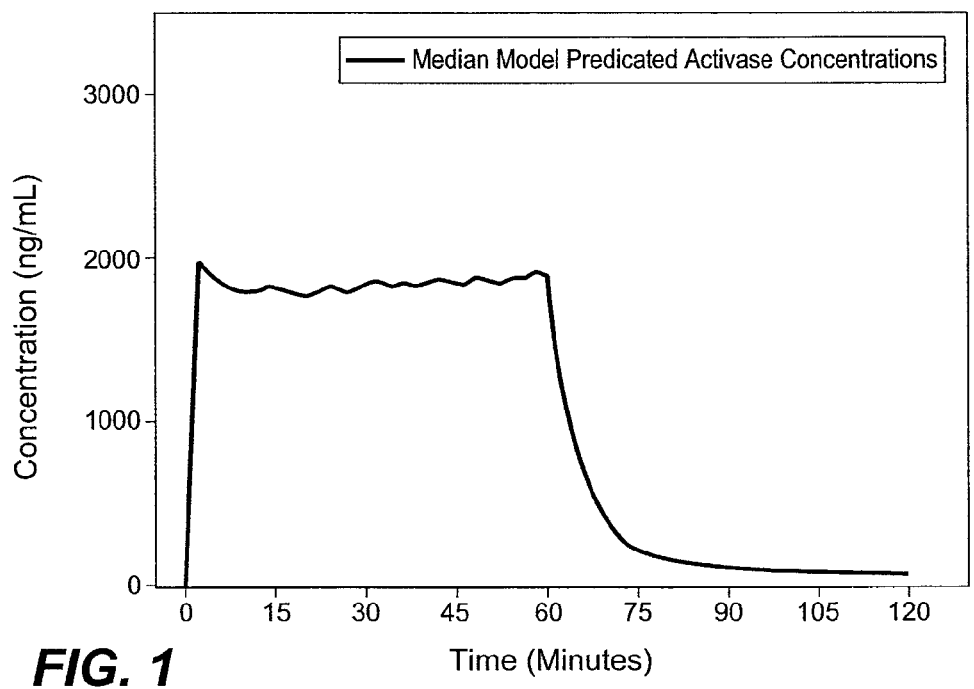
FIG. 1 shows median model-predicted ACTIVASE® (alteplase) concentrations after 0.9 m/kg as a 10% bolus over 1 minute and 90% over the remainder of 1 hour. These were the results of a 1000-subject simulation. Demographics were based on those observed in a pilot AIS stroke study.

"Stroke" is defined herein as a neurologic deficit caused by a cerebrovascular accident (CVA), which disrupts the blood supply to the brain for at least 24 hours. Stroke may take different forms, including hemorrhagic stroke and ischemic stroke, where each may be further subdivided. Thus, for example, hemorrhagic stroke may be characterized by a sudden development of neurological deficit with ICH or subarachnoid hemorrhage (SAH), while subtypes of ischemic stroke include lacunar, thromboembolic, and cardioembolic strokes. The term "stroke" is used herein in the broadest sense, and includes all forms of stroke, whether specifically listed herein or not.

"Transient ischemic attack" or "TIA" is defined herein as a temporary disruption in the blood supply to the brain, which is resolved completely within 24 hours, and usually lasts minutes to an hour.

"Acute ischemic stroke" is defined herein as an acute development of focal or global disturbance of cerebral function due to thromboembolism lasting more than 24 hours or leading to death. An acute focal ischemic stroke is damage to the brain caused by interruption of the blood supply to a region thereof. The acute ischemic stroke of interest herein is generally caused by obstruction of any one or more of the arteries, including the main cerebral arteries (e.g., middle cerebral artery, anterior cerebral artery, posterior cerebral artery, internal carotid artery, vertebral artery or basilar artery), and secondary arteries or arterioles. The "arterial obstruction." is generally a single embolus or thrombus or a plurality of clot particles that occlude primary and secondary arteries or arterioles.

The term "intraventricular hemorrhage" or "IVH" is used to refer to bleeding inside or around ventricles of brain. IVH is often classified in four grades: grade 1: bleeding occurs in a small area of the ventricles; grade 2: bleeding also occurs inside of the ventricles; grade 3: ventricles are enlarged by the blood; grade 4: bleeding extends into the brain tissue around the ventricles.

By "increasing cerebral blood flow or reducing infarct size" is meant the act of improving clinical outcome by inducing a statistically or physiologically significant increase in cerebral blood flow and/or a statistically or physiologically significant reduction in infarct size in a treated mammal relative to an untreated mammal as determined using techniques that are well known in the art, such as vascular imaging, for example. Preferably, cerebral blood flow as determined 2-4 hours after administration of the antagonist is increased by at least 30% and preferably at least 50% relative to an untreated mammal. Desirably, infarct size measured 48 hours after administration of the antagonist will be 20% less and preferably 50% less than that of an untreated mammal.

An "infarct" is an area of necrosis in a tissue or organ, for example, heart or brain, resulting from obstruction of the local circulation by a thrombus or embolus. Infarct size can be measured by known methods.

An "infarct-related artery" is an artery that, when at least partially blocked by a thrombus or embolus, gives rise to an infarct in a tissue or organ, for example, heart or brain.

"Treatment" refers to both therapeutic treatment and prophylactic or preventative measures. Those in need of treatment include those already with the disorder as well as those in which the disorder is to be prevented. Preferred herein is the treatment of those individuals who have been diagnosed as having suffered stroke, in particular, acute ischemic stroke.

As used herein, the term "tenecteplase," also known as TNK-tPA or TNKASE™ brand of tissue-plasminogen activator variant, refers to a tPA variant designated T103N, N117Q, K296A, H297A, R298A, R299A tPA available from Genentech, Inc. (South San Francisco Calif.) wherein Thr103 of wild-type tPA is changed to Asn (T103N), Asn 117 of wild-type tPA is changed to Gln (N117Q), and Lys-His-Arg-Arg (SEQ ID NO:1) 296-299 of wild-type tPA is changed to Ala-Ala-Ala-Ala (SEQ ID NO:2)(KHRR296-299AAAA). See the background section herein and U.S. Pat. No. 5,612,029.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

A "medicament" is an active drug to treat stroke or its symptoms or side effects.

A "second medicament" is one that can be added to help the first medicament, tenecteplase, to treat the stroke. Examples of such second medicaments include, without limitation, aspirin, intercellular adhesion molecule (ICAM)-1 and LFA-1 antagonists including antibodies such as enlimomab (an anti-ICAM-1 monoclonal antibody), and anti-CD18 and anti-CD11a antibodies, human anti-leukocytic antibodies such as Hu23F2G, glycoprotein IIb IIIa antagonists such as eptifibatide (INTEGRELIN™) (an intravenous cyclical heptapeptide that selectively blocks the platelet glycoprotein IIb/IIIa receptor), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenyloin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod (preferably intravenous, a fibrinogen-lowering agent derived from the venom of the Malayan pit viper), streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic-related neuroprotective activities, recombinant desmodus rotundus salivary plasminogen activator (rDSPA) alpha-1 (Schering/Teijin Pharmaceuticals), a mutant fibrin-activated human plasminogen (BB10153; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, an astrocyte-function-improving agent such as that disclosed in US 2004/0176347, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzene-disulfonate disodium n oxide), ebselen, glutathione peroxidase, norphenazone, rovelizurnab, lactacystin beta-lactone, tsukubaenolide, 4 phosphonomethylpipecolic acid, eliprodil, antibodies to ganglioside GM1, and biologically active variants, salts, and derivatives of any of the above.

A "thrombolytic agent" is a molecule that breaks up and/or dissolves a thrombus. Exemplary thrombolytic agents include streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al., (eds): *Hemostasis and Thrombosis* Lippincott, Philadelphia (1987) p. 886), tPA, and biologically active variants of each of the above. Suitable thrombolytic agents that may be used in this invention are disclosed, for example, in U.S. Pat. Nos. 5,770,425; 5,770,426; 5,612,029; 5,520,911; 5,736,134; 5,728,567; 5,714,145; 5,840,564; 5,616,486; 5,411,871; 5,520,913; 5,262,170; and 5,108,901.

"Co-administration" or "co-administering" as used herein means the administration of the second medicament during the effective therapeutic window of the tenecteplase administered alone. Thus, the second medicament may be administered before, concurrent with, or after the tenecteplase. Depending on the type of second medicament, the administration of the second medicament, such as anti-CD18 antibody, is preferably started from about 1 hour before up to immediately (1-15 minutes) before, more preferably concurrently with, the start of administration of the tenecteplase. Co-administration also encompasses administration of the second medicament after the start of administration of the tenecteplase, for example about 15-30 minutes after and up to about 3 hour after. Co-administration includes administration in the form of a single formulation, where the two medicaments may be, but do not have to be, physically separated from each other.

The "effective therapeutic window" of tenecteplase administered alone means the time period or time window following an infarct caused by blockage of an artery during which the tenecteplase, when administered alone, is effective in reestablishing patency of blood flow in the artery relative to a control not receiving the tenecteplase. The effective therapeutic window is species dependent for tenecteplase, but can be readily determined by standard tests evaluating the efficacy of the tenecteplase versus controls.

The term "anti-CD18 antibody" when used herein refers to an antibody that binds to CD18 (preferably human CD18) and inhibits or substantially reduces a biological activity of CD18. Normally, the antibody will block (partially or completely) the ability of a cell (e.g., a neutrophil) expressing the CD18 subunit at its cell surface to bind to endothelium.

Examples of anti-CD18 antibodies include MHM23 (Hildreth et al. (1983)); M18/2 (IgG$_{2a}$; Sanches-Madrid et al., *Eur. J. Immunol.* 13(3):202-208 (1983)); H52 (American Type Culture Collection (ATCC) Deposit HB 10160); Mas191c and IOT18 (Vermot Desroches et al., *Scand. J. Immunol.* 33(3):277-286 (1991)); and NA-8 (WO 94/12214). The preferred antibody is one that binds to the CD18 epitope to which either MHM23 or H52 binds. Preferably the antibody has a high affinity for the CD18 polypeptide. In preferred embodiments, the antibody has an affinity for the CD antigen of about 4 nM or less. Preferably, the affinity is about 3 nM or less, and most preferably about 1 nM or less. In certain embodiments, the antibody may bind to a region in the extracellular domain of CD18 that associates with CD11b and the antibody may also dissociate alpha and beta chains (e.g., the antibody may dissociate the CD11b and CD18 complex, as is the case for the MHM23 antibody).

MODES FOR CARRYING OUT THE INVENTION

In addition to early intervention, the outcome of the treatment of stroke with thrombolytic agents, such as tenecteplase, and the survival and recovery of stroke patients following treatment are closely related to the manner in which the thrombolytic therapy is administered. The present invention provides an improved protocol for the treatment of stroke, in particular acute ischemic stroke, with tenecteplase. The treatment protocols and dosing regimens of the present invention result in pharmacokinetic profiles that offer maximum efficacy and safety, and thus represent a significant advance in the thrombolytic therapy of stroke.

In one aspect, the invention provides a method for treating acute ischemic stroke in a human comprising administering to the human tenecteplase in a total dose of about 0.05 to 0.15 mg/kg (preferably about 0.2 to 0.3 mg/kg, and more preferably about 0.25 mg/kg), given as an initial dose of about 0.015 to 0.15 mg/kg bolus (preferably about 0.08 to 0.12 mg/kg bolus, more preferably about 0.1 mg/kg bolus), followed by infusion of the remaining amount to total about 0.05 to 0.5 mg/kg (preferably about 0.2 to 0.3 mg/kg, more preferably about 0.25 mg/kg) over a period of about 50-90 minutes, more preferably about 55-70 minutes, and most preferably about 60 minutes. For example, if the total dose is about 0.25 mg/kg tenecteplase, then the initial bolus dose is preferably about 0.1 mg/kg and the subsequent infusion is about 0.15 mg/kg. Based on current experiments, this is the most preferred regimen, wherein the subsequent infusion is given over about 60 minutes. It is noted, however, that the most preferred dosing schedule might vary within the specified dosing ranges, depending on various factors, including the specific type and extent of stroke, the condition of the patient, the time elapsed from the onset of stroke, and the like.

The infusion of tenecteplase may follow immediately after the bolus dose is complete, or can be separated from completion of the bolus dosage by up to about 30 minutes, but it is preferred to initiate the infusion immediately after the bolus dose is completed. Preferably, the bolus injection is intravenous, but it may be injected by other means such as intra-arterially. Preferably, the infusion is continuous by intravenous, intramuscular, intraperitoneal, intracerebrospinal, subcutaneous, intra-articular, intrasynovial, or intrathecal routes, but the preferred infusion is intravenous.

In an alternative aspect, acute ischemic stroke is treated in a human by administering tenecteplase in a total dose of about 0.05 to 0.15 mg/kg, preferably about 0.2 to 0.3 mg/kg, more preferably about 0.25 mg/kg, given exclusively as a bolus dose. Preferably, the bolus is intravenous.

Stroke is a serious condition and the third leading cause of death in the United States. Since survival and the extent of recovery are a function of the time of diagnosis and intervention, in the methods of the present invention it is contemplated that the tenecteplase will be administered to a patient as soon as possible once the condition of acute ischemic stroke has been diagnosed or is suggested by acute deficit on neurologic examination.

Initial clinical presentations of acute ischemic stroke typically include one or more of (1) alterations in consciousness, such as stupor or coma, confusion or agitation, memory loss, seizures, and/or delirium; (2) headache that is intense or unusually severe, is associated with decreased level of consciousness/neurological deficit, and/or includes unusual/severe neck or facial pain; (3) aphasia (incoherent speech or difficulty understanding speech); (4) facial weakness or asymmetry; (5) uncoordination, weakness, paralysis, or sensory loss of one or more limbs; (6) ataxia (poor balance, clumsiness, or difficulty walking); (7) visual loss; and (8) intense vertigo, double vision, unilateral hearing loss, nausea, vomiting and/or photophobia. The presence of one or more of these manifestations might be an initial indication of acute ischemic stroke, which can be verified by follow-up differential diagnosis and neurological examination.

Neurologic examination and, optionally, neuroimaging techniques such as computed tomography (CT) (including non-contrast CT and perfusion CT) and magnetic resonance imaging (MRI) (including diffusion weighted imaging (DWI) and perfusion imaging (PI)); vascular imaging (e.g., duplex scanning and transcranial Doppler ultrasound and laser Doppler); and angiography (e.g., computerized digital subtraction angiography (DSA) and MR angiography) as well as other invasive or non-invasive techniques, are available for the diagnosis of acute ischemic stroke.

There are several scales available to assess the severity of stroke. These include the Barthel Index (Mahoney and Barthel, *Maryland State Medical Journal,* 14:56-61 (1965)), the Modified Rankin Scale (Rankin, *Scot. Med., J.* 2:200-215 (1957); van Swieten et al., *Stroke,* 19: 604-607 (1988); Duncan et al., *Stroke,* 31: 1429-1438 (2000)), the Glasgow Outcome Scale (Jennett and Bond, *Lancet,* 1(7905):480-4 (1975); Teasdale, *J. Neuro. Neurosurg. Psychiatry,* 41:603-610 (1978); Jennett et al., *Lancet,* 1:480-484 (1995)), and the National Institute of Health Stroke Scale (NIHSS) (Brott et al., *Stroke,* 20: 864-870 (1989)). The methods of the present invention are suitable for the treatment of acute ischemic stroke of all stages of severity.

Preferably, the tenecteplase will be administered in the dosage and dosage regimen herein at least once at any time from immediately following to about 24 hours after the onset of stroke. In certain embodiments, the tenecteplase is first administered to the patient between about 15 minutes (or about 30 or 45 minutes) to about 20 hours (more preferably about 10 hours, or about 6 hours, or 3 hours, or about 90 minutes, or about 60 minutes) from the onset of stroke. In a particular embodiment, a patient presenting within 3 hours of the onset of signs and symptoms consistent with an acute ischemic stroke is subjected to thrombolytic therapy with tenecteplase in accordance with the present invention.

In the method herein, one may administer to the patient along with the tenecteplase an effective amount of a second medicament (where the tenecteplase is a first medicament).

The second medicament may be one or more medicaments, and may include, for example, those set forth above. Preferred such medicaments include neuroprotective agents, anticonvulsive agents, a spin-trap agent, intercellular adhesion molecule (ICAM)-1 and LFA-1 antagonists such as anti-CD11a and anti-CD18 antibodies, glycoprotein IIb IIIa antagonists, neuronal wound healing agent, antibodies inhibiting platelet aggregation and adhesion, and human anti-leukocytic antibodies, or another thrombolytic agent than tenecteplase. More preferred are neuroprotective agents, other thrombolytic agents, glycoprotein IIb IIIa antagonists, and anti-CD18 antibodies.

These second medicaments are generally used in the same dosages and with administration routes as used hereinbefore or about from 1 to 99% of the heretofore-employed dosages. If such second medicaments are used at all, preferably, they are used in lower amounts than if the tenecteplase were not present, especially in subsequent dosings beyond the initial dosing with tenecteplase, so as to eliminate or reduce side effects caused thereby.

Where a second medicament is administered in an effective amount with a tenecteplase bolus dosing, it may be administered with any such dosing, for example, only with one such dosing, or with more than one such dosing. In one embodiment, the second medicament is administered with the initial bolus dosing. In another embodiment, the second medicament is administered with the first and second dosings. In a still further embodiment, the second medicament is administered with all tenecteplase dosings.

The combined administration includes co-administration (concurrent administration), using separate formulations or a single pharmaceutical formulation, and consecutive administration in either order, wherein preferably there is a time period while both (or all) active agents simultaneously exert their biological activities. It is preferred that after the initial exposure, the amount of such agent is reduced or eliminated so as to reduce the exposure of the subject to an agent with side effects such as prednisone and cyclophosphamide.

In addition, a device such as an INTERCOOL™ device and/or using external ice at 33° C. or a similar temperature may be employed along with the tenecteplase for treating the stroke.

Therapeutic formulations of the tenecteplase are prepared for storage by mixing the tenecteplase having the desired degree of purity with optional physiologically acceptable carriers, excipients or stabilizers (*Remington's Pharmaceutical Sciences* 16th edition. Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; amino acids such as glycine, glutamine, asparagine, histidine, arginine or lysine; monosaccharides, disaccharides and other carbohydrates including glucose, mannose, trehalose or dextrins; chelating agents such as EDTA; sugar alcohols such as mannitol or sorbitol; salt-forming counterions such as sodium; and/or nonionic surfactants such as TWEEN™, PLURONICS™ or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes, prior to or following lyophilization and reconstitution.

Sustained-release preparations may be employed. Suitable examples of sustained-release preparations include semipermeable matrices of solid hydrophobic polymers containing the tenecteplase, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release tenecteplase compositions also include liposomally entrapped tenecteplase. Liposomes containing the tenecteplase are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal tenecteplase therapy. Liposomes with enhanced circulation time are disclosed in U.S. Pat. No. 5,013,556.

The exact total dosage of tenecteplase to be employed, and how much is by bolus and how much by infusion, or whether only bolus should be employed, will depend, for example, on the exact nature of the stroke to be treated, the severity and course of the stroke, whether the tenecteplase is administered for preventive or therapeutic purposes, previous therapy, the patient's clinical history and response to the tenecteplase, and the discretion of the attending physician. The progress of this therapy is easily monitored by conventional techniques and assays elaborated herein.

In another embodiment of the invention, there are provided articles of manufacture and kits containing materials useful for improving clinical outcome in stroke. The article of manufacture comprises a container with a label. Suitable containers include, for example, bottles, vials, and test tubes. The containers may be formed from a variety of materials such as glass or plastic. The container holds a composition that is effective for treating stroke as defined herein and may have a sterile access port (for example, the container may be an intravenous solution bag or a vial having a stopper pierceable by a hypodermic injection needle). The active agent in the composition is tenecteplase. The label on the container indicates that the composition is used for treating stroke as described above, and may also indicate directions for in vivo use, such as those described above.

Specifically, in one embodiment, the kit comprises a container comprising tenecteplase and instructions for using the tenecteplase to treat acute ischemic stroke in a human by administering the tenecteplase to the human in a total dose of about 0.05 to 0.5 mg/kg, given as (a) an initial bolus dose of about 0.015 to 0.15 mg/kg, followed by infusion of an amount equaling the total dose minus the initial dose over a period of about 50-90 minutes, or (b) a bolus. Preferably, the total dose is about 0.2 to 0.3 mg/kg, more preferably about 0.25 mg/kg, and the initial dose under option (a) above is about 0.08 to 0.12 mg/kg, more preferably about 0.1 mg/kg.

In one embodiment of the kit, the total dose is given as an initial bolus followed by the infusion. In a preferred embodiment, the total dose is about 0.25 mg/kg, given as an initial about 0.1 mg/kg bolus, followed by infusion of about 0.15 mg/kg over about 60 minutes.

In another embodiment of the kit, the total dose is given as a bolus.

These kits may optionally also comprise a container holding a second medicament, wherein the instructions include directions for using the second medicament in combination with the tenecteplase to treat ischemic stroke in a human by administering to the human an effective amount of the second medicament. Exemplary second medicaments and preferred second medicaments are noted above.

The kits of the invention may also comprise another container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The following example is offered by way of illustration and not by way of limitation. The disclosures of all citations in the specification are expressly incorporated herein by reference.

EXAMPLE

Determination of Dosing Regimen of Tenecteplase for the Treatment of Acute Ischemic Stroke A dosing strategy that improves the safety and efficacy of the treatment of AIS with tenecteplase was developed by performing PK modeling.

It has been established that efficacy outcomes with thrombolytics are related to dose and concentration for both ACTIVASE® (alteplase) (Gulba et al. *J. Am. Coll. Cardiol.*, 30/7 1611-1617 (1997); Tanswell et al., *J. Am. Coll. Cardiol.*, 19/5 1071-1075 (1992)) and TNKase (tenecteplase) (Wang-Clow et al., *Am Heart J.*, 141/1 33-40 (2001); Tanswell et al., *Clin. Pharmacokinet.*, 41/15 1229-45 (2002)). This observation suggested that a PK-based approach to dose selection with thrombolytics would be appropriate. Furthermore, PK analysis of a rabbit in-vivo PK and pharmacodynamic (PD) study suggested that alteplase and TNKase were approximately equipotent when comparing the area under the curve (AUC) and time to 50% clot lysis (Thomas et al. *Stroke*, 25/10 2072-2078 (1994)). This was also inferred from the TIMI10B clinical study of AMI patients treated with alteplase and TNKase, where not only the efficacy and safety outcomes were found to be similar, but also the concentrations of alteplase and TNKase at the key treatment time-points of 30 minutes and 90 minutes. These time points were important because they marked the change in infusion rate and termination of infusion of alteplase, respectively (Modi et al., *J. Clin. Pharm.*, 40/5: 508-515 (2000)). From this, it was concluded that a TNKase dosing regimen that recapitulates the concentration time profile as well as the exposure of alteplase during the treatment period (0-60 minutes) would result in similar efficacy and potentially improved safety in AIS because of the relationship between drug concentration and response, and because of similar efficacy at similar concentrations.

Accordingly, PK modeling was performed using historical alteplase acute myocardial infarct (AMI) PK data as well as TNKase data in AMI and stroke to an provide appropriate dose of TNKase for AIS. Based on the PK modeling, a dose of 0.25 mg/kg given as an initial 0.1 mg/kg bolus, followed by 0.15 mg/kg infusion over 60 min, was the preferred regimen. A bolus of 0.25 mg/kg bolus was the 2nd choice for a TNKase dose in AIS dosing strategy.

The TNKase dosing regimens were derived using a modeling and simulation approach intended to recapitulate the exposure and concentration time profile of alteplase during the treatment period associated with the USPI dosing of 0.9 mg/kg (10% bolus over 1 minute and 90% over the remainder of an hour). This required building an alteplase structural and error model (PK model) based on published PK parameters and concentrations, and constructing the TNKase population PK model (PPK model) from in-house AMI and AIS PK data.

All calculations were performed using the NONMEM modeling software package Version 5 (Beal, Boeckman, and Sheiner NONMEM user's guide, 1988-1992. 1992. San Francisco, Calif., University of California at San Francisco). Alteplase has been described as following two- and three-compartment PKs (Seifried et al., *Thrombosis & Haemostasis*, 61/3: 497-501 (1989); Tanswell et al., *Arzneimittelforschung*, 41/12: 1310-19 (1991); Tanswell et al., *Clin. Pharmacol. Ther.*, 46/2: 155-62 (1989); Tanswell et al., *J. Amer. College of Cardiology.* 19/5: 1071-75 (1992); Tebbe et al., *The American Journal of Cardiology*, 64/8: 448-53 (1989)). A two-compartment model was chosen because it was described in the literature most recently, and with the more commonly used front-loaded dosing regimen (Neuhaus et al., *J. Am. Coll. Cardiol.*, 19/5: 885-891 (1992)). PK parameters as well as the mean and standard deviation of the concentrations at 30 and 90 minutes were also used (Tanswell et al., *J. Am. Coll. Cardiol*, 19/5: 1071-75 (1992)). While the model was based on PK associated with the AMI dosing regimen for alteplase, the PK parameters were considered reasonable approximations for use in simulating concentrations that would be achieved with the USPI dosing of alteplase for AIS (Genentech). The final alteplase PK model parameters used for simulations are summarized in Table I.

TABLE I

| Alteplase PK Parameters | |
| --- | --- |
| Parameter | Model Result Parameter Estimate (CV) |
| Typical CL | 518 mL/min (23%) |
| Typical Volume | 3100 mL (20%) |
| K12 | 0.0271 min$^{-1}$ (0%) |
| K21 | 0.0113 min$^{-1}$ (0%) |

The TNKase PPK model was derived using individual patient serum concentration data from the AMI trial TIMI10B (Modi et al., supra) and a pilot dose-escalating AIS trial. The combined data were best described using a two-compartment model. The final model results are summarized in Table II.

TABLE II

TNKase (Tenecteplase) Final Model Estimates

| Parameter | Model Result Parameter estimate (SEE) |
|---|---|
| Method | FOCE with INTER |
| No. of Concentrations | 830 |
| Objective Function | 9778 |
| Typical CL | 106 mL/min (3%) |
| Wt on CL | 0.377 (24%) |
| Age on CL | −0.200 (40%) |
| Typical Vc | 4070 mL (4.7%) |
| K12 | 0.00249 min−1 (13%) |
| K12 | 0.0102 min−1 (8.7%) |
| Baseline | 18.1 ng/mL (4.9%) |
| ω CL | 14.7% (28%) |
| ωVc | 15.4% (47%) |
| ω Baseline | 33.3% (22%) |
| σ prop | 31.5% (1.0%) |
| σ add | ~0 mg/mL |
| K10 | 0.02604 day−1 |

Because the TNKase PK assay did not distinguish endogenous tPA from administered TNKase, a baseline parameter was included in the model to capture endogenous tPA levels. Weight and age were included as covariates on clearance (CL) according to the formula:

$$CL_j = \hat{CL}(WT_j/81.8)^{0.377}(AGE_j/58)^{-0.200}$$

$\hat{CL}$ is the population estimate of CL, $CL_j$ is the individual CL, $WT_j$ is the individual weight with 81.8 as the median weight, and $AGE_j$ is the individual age with 58 as the median age. The TNKase PPK model was then used for AIS dosing regimen estimates and simulations of candidate dosing regimens in an effort to produce similar concentration-time profiles and exposure that was predicted for alteplase.

The basis for the TNKase dosing regimens was the concentration-time profile and exposure of the USPI dosing regimen for alteplase during the 60-minute treatment period (FIG. 1). The strategy was to use this as an approximate target for TNKase dosing. FIG. 1 suggested that the 10% alteplase bolus results in near steady-state drug concentrations, followed by a fairly constant concentration of alteplase for the remaining 60 minutes. Model-estimated median concentration values obtained at two-minute intervals from 2-60 minutes were then used to calculate mean effective concentration (computer program JMP version 5.1. 2003) (SAS Institute Inc) and the AUC.

Based on the observed time-concentration profile, the first TNKase regimen for stroke included a bolus followed by a constant infusion. The required bolus dose to get to the mean effective concentration was derived by the following formula:

$$\text{Bolus dose} = \hat{V}d \times C_{effective}$$

Where:

$\hat{V}d$ = population volume $C_{effective}$ = alteplase mean effective concentration The alteplase mean effective concentration and TNKase $\hat{V}d$ (population Volume) were ~1800 ng/mL and 4072 ml., respectively, requiring an approximate TNKase bolus dose of 01047 mg/kg.

The alteplase exposure was defined as the AUC 0-60 minutes. The TNKase dose required to obtain a similar exposure during the 60-minute dosing period was derived from the following formula:

$$\text{Total } TNKase \text{ Dose} = \frac{AUC_{Activase}}{\hat{CL}_{TNKase}}$$

Where:

$AUC_{Activase}$ = Alteplase AUC during the 0-60 minute treatment period $\hat{CL}_{TNKase}$ = TNKase population Clearance The alteplase AUC during the 60-minute dosing period was calculated by the following formula:

$$\text{Alteplase AUC} = C_{effective} \times 60 \text{ minutes}$$

Where:

$C_{effective}$ = Mean alteplase effective concentration from 0-60 minutes

The mean effective concentration for alteplase was approximately 1800 ng/mL resulting in an AUC of 108,000 ng*min/mL. With the TNKase population clearance of 105 mL/min, the total TNKase dose required to maintain a concentration and exposure approximating the effective concentration was 0.16 mg/kg administered over 1 hour.

Figure 2:
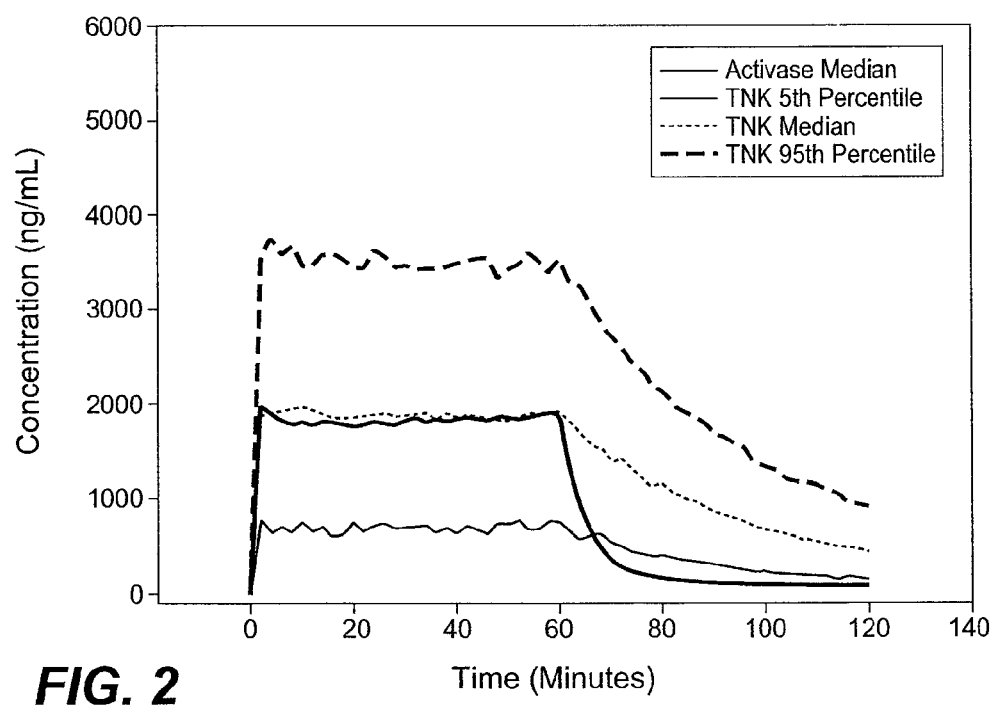
FIG. 2 shows model-predicted pharmacokinetic (PK) profiles from 1000-subject simulations comparing the median model-predicted alteplase (ACTIVASE®) concentrations with the model-predicted tenecteplase (TNK) median, $5^{th}$, and $95^{th}$ percentile concentrations from a 0.25 mg/kg bolus-infusion regimen. The simulation was based on TNKase administered as 0.25 mg/kg as 0.1 mg/kg bolus over 1 minute, 0.15 mg/kg over remainder of one hour. TNK $5^{th}$ Percentile is the lowest (and solid) line on the graph, TNK Median is the dotted line close to the Activase Median line, and TNK $95^{th}$ Percentile is the uppermost dashed line. The median model-predicted alteplase concentration was based on 0.9 mg/kg (90 mg/kg max) as 10% bolus and 90% over the remainder of one hour (Activase Median is the solid line that plateaus and then drops off after 60 minutes).

A more clinically applicable dose of 0.1 mg/kg bolus and 0.15 mg/kg infusion over 60 minutes was identified from the calculated 0.1047 mg/kg bolus dose and 0.16 mg/kg 60-minute infusion and tested in a 1000-subject simulation. FIG. 2 shows how the mean, $5^{th}$, and $95^{th}$ percentile concentrations from this regimen compared to the model-predicted concentrations for alteplase.

The AUC for the treatment period of 0-60 minutes, post-treatment periods of 60-120 minutes, and overall AUC from 0-120 minutes were calculated using the computer program WinNonlin version 3.0 2001 (WinNonlin) and summarized in Table III.

TABLE III

AUC and Concentration Comparisons For TNKase
0.25 mg/kg Bolus/Infusion Dosing Regimen

| | Alteplase | | 0.25 mg/kg TNKase | | |
|---|---|---|---|---|---|
| | AUC* (Median) | % AUC | AUC* (Median) | % AUC | % Alteplase AUC |
| AUC (0-60) | 107941 | 87 | 111102 | 66 | 103 |
| AUC (60-120) | 15487 | 13 | 57809 | 34 | 376 |
| AUC (0-120) | 123428 | 100 | 168911 | 100 | 137 |

| | Median Concentrations | |
|---|---|---|
| | Alteplase | 0.25 mg/kg TNKase |
| $C_{2\,minutes}$ | 1959 | 1934 |
| $C_{30\,minutes}$ | 1824 | 1874 |
| $C_{60\,minutes}$ | 1871 | 1877 |

*AUC = Area under the curve

Based on these results, a dose of TNKase of 0.25 mg/kg administered as 0.1 mg/kg bolus over 1 minute and 0.15 mg/kg over the remainder of 1 hour was determined as an appropriate dosing regimen for TNKase in AIS.

Additional dosing regimens were considered to determine if outcomes could be enhanced. In the clinical studies leading to the approval of alteplase in stroke, bleeding was the dose-limiting toxicity. However, the AMI literature suggested that higher concentrations of thrombolytics may improve clot lysis. This relationship of exposure to response was observed in at least two studies where alteplase was administered as a front-loaded dosing regimen, resulting in improved outcomes in AMI (Gulba et al., supra; Neuhaus et al., supra). Because the fibrin specificity of TNKase could theoretically allow higher doses with less effect on fibrinogen and subsequent risk of bleeding, a bolus dosing regimen of 0.25 mg/kg was considered. The intent was to administer higher early doses to improve clot lysis (consistent with what has been observed with alteplase in AMI) without altering fibrinogen or increasing the risk of bleeding. This bolus regimen also would reduce the low-level exposure at later time points observed with the bolus-infusion regimen.

Figure 3:
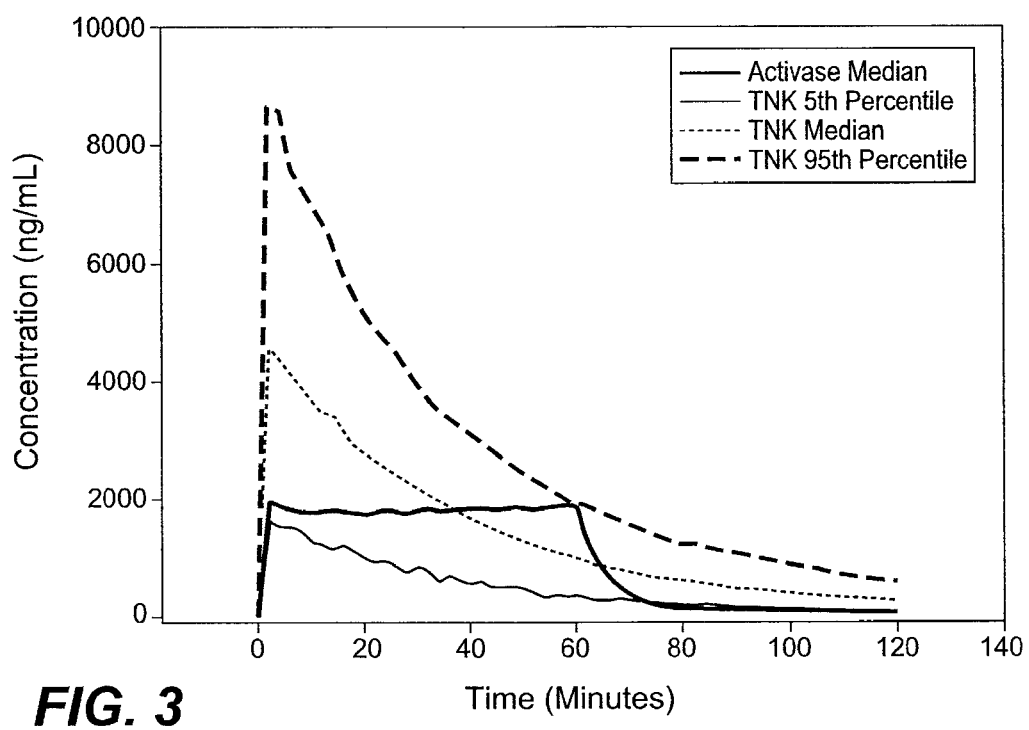
FIG. 3 shows model-predicted PK profiles from 1000-subject simulations comparing the median model-predicted alteplase (ACTIVASE®) concentrations for a bolus-infusion regimen with the model-predicted tenecteplase (TNK) median, $5^{th}$, and $95^{th}$ percentile concentrations from a 0.25 mg/kg bolus-only regimen. TNK $5^{th}$ Percentile is the lowest (and solid) line on the graph, TNK Median is the dotted line above the Activase Median line, and TNK $95^{th}$ Percentile is the uppermost dashed line. The median model-predicted alteplase concentration was based on 0.9 mg/kg (90 mg/kg max) as 10% bolus and 90% over the remainder of one hour (Activase Median is the solid line that plateaus and then drops off after 60 minutes).

FIG. 3 shows the median model-predicted alteplase concentrations with the model-predicted TNKase median, $5^{th}$, and $95^{th}$ percentile concentrations from the 0.25 mg/kg bolus regimen. Table IV summarizes the AUC values and compares concentrations at key timepoints. Overall, the exposure and concentration time curves observed from simulating a 0.25 mg/kg bolus suggested that this regimen for bolus-only treatment was appropriate.

TABLE IV-continued

AUC and Concentration Comparisons For TNKase 0.25 mg/kg Bolus-Only Dosing Regimen

| | Median Concentrations | |
|---|---|---|
| | Alteplase | 0.25 mg/kg TNKase |
| $C_{2\ minutes}$ | 1959 | 4595 |
| $C_{30\ minutes}$ | 1824 | 2163 |
| $C_{60\ minutes}$ | 1871 | 1002 |

In summary, bolus-infusion and bolus-only dosing regimens of TNKase for use in treating acute ischemic stroke were determined using pharmacokinetic modeling and simulation. These dosing regimens were designed to provide improved safety and efficacy from tenecteplase as compared to alteplase when administered to AIS patients.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by letters patent hereon be limited only by the appended claims and equivalents thereof.

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Lys His Arg Arg
 1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Ala Ala Ala Ala
 1
```

TABLE IV

AUC and Concentration Comparisons For TNKase 0.25 mg/kg Bolus-Only Dosing Regimen

| | Alteplase | | 0.25 mg/kg TNKase | | |
|---|---|---|---|---|---|
| | AUC* (Median) | % AUC | AUC* (Median) | % AUC | % Alteplase AUC |
| AUC (0-60) | 107941 | 87 | 140191 | 81 | 130 |
| AUC (60-120) | 15487 | 13 | 33242 | 19 | 215 |
| AUC (0-120) | 123428 | 100 | 173433 | 100 | 141 |

What is claimed is:

1. A method for treating acute ischemic stroke in a human comprising administering tenecteplase to the human in a total dose of about 0.05 to 0.5 mg/kg, given as an initial bolus dose of about 0.05 to 0.15 mg/kg, followed by infusion of an amount equaling the total dose minus the initial dose over a period of about 50-90 minutes.

2. The method of claim 1 wherein the total dose is about 0.2 to 0.3 mg/kg.

3. The method of claim 1 wherein the total dose is about 0.25 mg/kg.

4. The method of claim 1 wherein the initial dose is about 0.08 to 0.12 mg/kg bolus.

5. The method of claim 1 wherein the initial dose is about 0.1 mg/kg bolus.

6. The method of claim 1 wherein the period of infusion is about 55-70 minutes.

7. The method of claim 1 wherein the period of infusion is about 60 minutes.

8. The method of claim 1 wherein the total dose is about 0.25 mg/kg, given as an initial bolus of about 0.1 mg/kg, followed by infusion of about 0.15 mg/kg over about 60 minutes.

9. The method of claim 1 wherein the tenecteplase is administered to the human at a time between about 15 minutes and 20 hours from the onset of acute ischemic stroke.

10. The method of claim 1 wherein the tenecteplase is administered to the human at a time between about 30 minutes and 6 hours from the onset of acute ischemic stroke.

11. The method of claim 1 wherein the tenecteplase is administered to the human at a time between about 30 minutes and 3 hours from the onset of acute ischemic stroke.

12. The method of claim 1 wherein the bolus is intravenous.

13. The method of claim 1 further comprising administering to the human an effective amount of a second medicament, wherein the first medicament is tenecteplase.

14. The method of claim 13 wherein the second medicament is a neuroprotective agent, a thrombolytic agent, a glycoprotein IIb IIIa antagonist, or an anti-CD18 antibody.

* * * * *